United States Patent [19]

Mears

[11] Patent Number: 4,982,850
[45] Date of Patent: Jan. 8, 1991

[54] TEST-TUBE HOLDER WITH SAFETY SHIELD

[76] Inventor: Donald B. Mears, 31 Locke Dr., Enfield, Conn. 06082

[21] Appl. No.: 372,320

[22] Filed: Jun. 28, 1989

[51] Int. Cl.$^5$ .................................................. A47F 7/00
[52] U.S. Cl. ...................................... 211/74; 604/192; 604/263
[58] Field of Search ................... 211/74; 604/192, 263; 422/102, 104; 206/365, 366, 367, 443

[56] References Cited

U.S. PATENT DOCUMENTS

| | | |
|---|---|---|
| 3,175,695 | 3/1965 | Goodman et al. . |
| 3,186,556 | 6/1965 | Forsstrom . |
| 3,905,482 | 9/1975 | Knulst . |
| 3,905,772 | 9/1975 | Hartnett et al. ................. 211/74 X |
| 4,278,176 | 7/1981 | Adams . |
| 4,510,119 | 4/1985 | Hevey ............................. 211/74 X |
| 4,534,465 | 8/1985 | Rothermel et al. . |
| 4,573,975 | 3/1986 | Frist et al. . |
| 4,717,386 | 1/1988 | Simmons . |
| 4,742,910 | 5/1988 | Staebler . |
| 4,840,618 | 6/1989 | Marvel ........................... 604/192 X |

Primary Examiner—Robert W. Gibson, Jr.
Attorney, Agent, or Firm—Donald S. Holland

[57] ABSTRACT

An improved hand-held test-tube holder is disclosed. It is a safety device to prevent the contraction by health-care professionals of Acquired Immune Deficiency Syndrome (AIDS), when dealing with infected blood samples. In the preferred embodiment, the invention comprises an oval base; a plurality of vertical shafts for housing vials; and an overlying, horizontal shield. The shield is designed to completely cover the user's cupped hand that grasps the shafts and lifts the holder. It thereby protects that hand from being accidentally pricked by a contaminated needle during the process of drawing blood from an infectious sample in a vial housed in the holder, or during the similar process of depositing a sample into the vial.

7 Claims, 3 Drawing Sheets

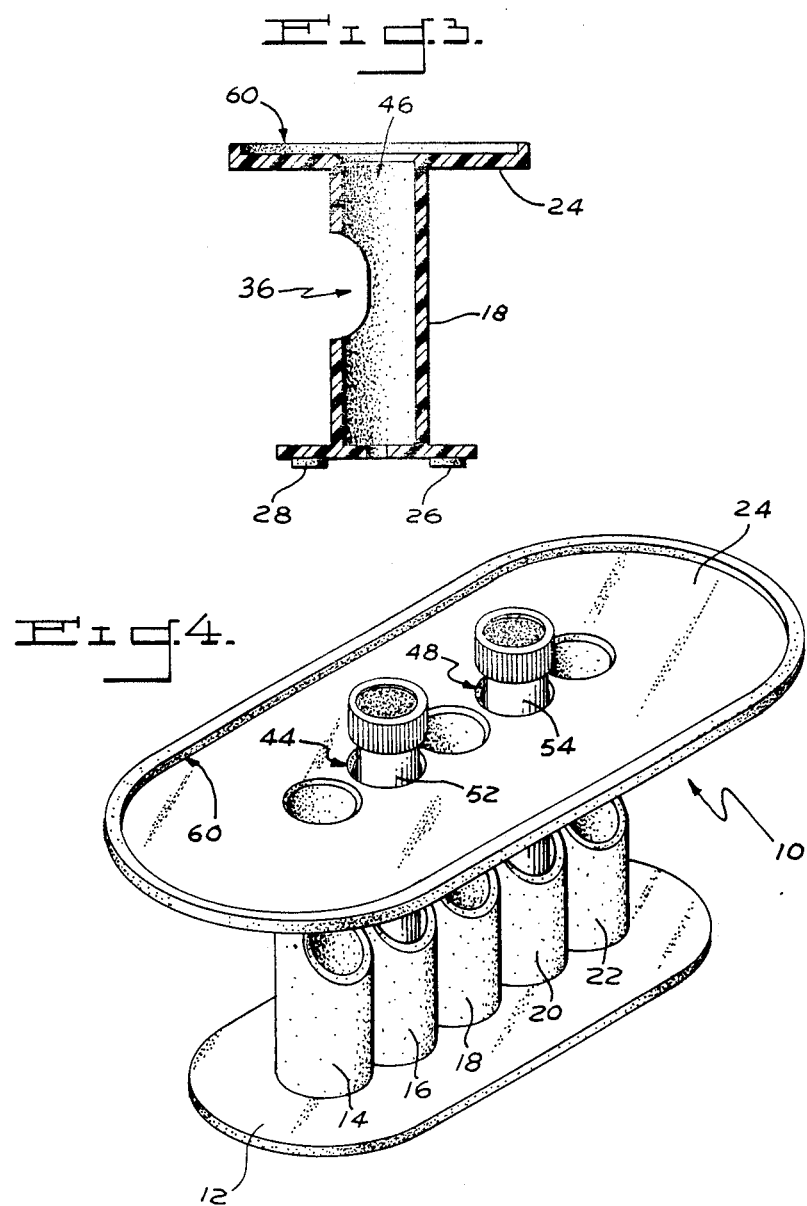

TEST-TUBE HOLDER WITH SAFETY SHIELD

BACKGROUND OF THE INVENTION

The present invention relates to products for preventing the contraction and spread of Acquired Immune Deficiency Syndrome (AIDS). More particularly, it deals with safety devices used by lab technicians to reduce the risks of accidental needle-pricks which are capable of spreading the disease.

History is filled with epidemics, such as the Black Plague, that have literally attacked thousands of people. AIDS is a modern epidemic that must be controlled. Appropriate steps to prevent contraction of the disease require education and safety measures.

AIDS is a disease caused by a virus that attacks the body's immune system, leaving it vulnerable to certain types of infections. It is the subsequent infection that will eventually kill the victim, not the AIDS disease. Once a victim becomes infected with the disease, he remains infectious for life. Groups typically struck by AIDS include young adults, but especially homosexuals and intravenous (IV) drug abusers.

At the present time there is no known certified cure for AIDS. Initially, public fear ran rampant with possible ways of contracting the disease, such as casual contact or through sneeze or cough droplets; however, there is no evidence to support this. Now it is recognized that AIDS can be transmitted only through sexual intercourse with an infected partner; through contact with contaminated needles or syringes; or exposure to infected blood or blood products.

Because AIDS can be transmitted by needles and syringes which contain the virus, great care must be exercised by health-care professionals to prevent accidental needle-prick injuries when working with potentially infectious blood samples. If a health-care professional, such as a lab technician, is working with a vial that contains an AIDS sample and he accidentally scrapes himself with a contaminated needle that contains a sample from that vial, he runs the risk of catching AIDS. Because these health-care professionals are subject to the same fears as the public at large and because they may work with many potentially infectious blood samples on a daily basis, extra precautions are necessary to prevent their contraction of AIDS and to alleviate their fears.

There are many test-tube holders that stand independently and permit vials to be stored. However, none of them can be hand-held conveniently to draw blood from a stored vial without the fear of needle-pricks.

For example, U.S. Pat. No. 4,278,176 to Adams allows multiple test tubes to be placed in a rack and is capable of being hand-held. It also has both an upper ledge or "shield" and two side ledges. These ledges, however, afford little protection to the user. For instance, if this test-tube rack is hand-held, with the hand placed on the outer side of ledges, the user's hand is still exposed to the risk of needle-pricks. Should his needle miss the test tube and strike the "shield", it is possible for the needle to continue along the "shield" until it strikes the user's hand.

Although this rack is capable of being grasped from underneath, therefore providing protection from needle-pricks, it was not designed as such and would be awakard to use in that manner. For example, lifting and returning the test-tube holder would require the user to first grasp it with his hand on the outside and then transfer it to his other hand, which would grasp it from the underneath.

Accordingly, it is the primary object of the present invention to provide an improved test-tube holder which overcomes the deficiencies of the prior art.

It is a general object to provide a test-tube holder that prevents lab technicians from contracting AIDS through accidental needle-pricks during removal of a blood sample from a vial which contains an AIDS sample; this will alleviate his fears so that he may be better able to concentrate on his assigned task.

It is still another object to provide a clear test-tube holder which allows the user to actually see the amount remaining in the vial without removing the vial or tilting the test-tube holder.

It is yet another object to allow the user to physically manipulate the vials while the vials are in their appropriate shaft. Because the user can press the vial against the back of the shaft, he can hold the vial steady while he attempts to insert and remove the needle.

The above and other objects and advantages of this invention will become more readily apparent when the following description is read in conjunction with the accompanying drawings.

BRIEF DESCRIPTION OF THE DRAWINGS

FIG. 3 is a side plan view of the test-tube holder taken along line 3—3 of FIG. 1;

FIG. 4 is a top perspective view, similar to FIG. 1, with two test tubes inserted.

DETAILED DESCRIPTION OF THE PREFERRED EMBODIMENTS

Figure 1:
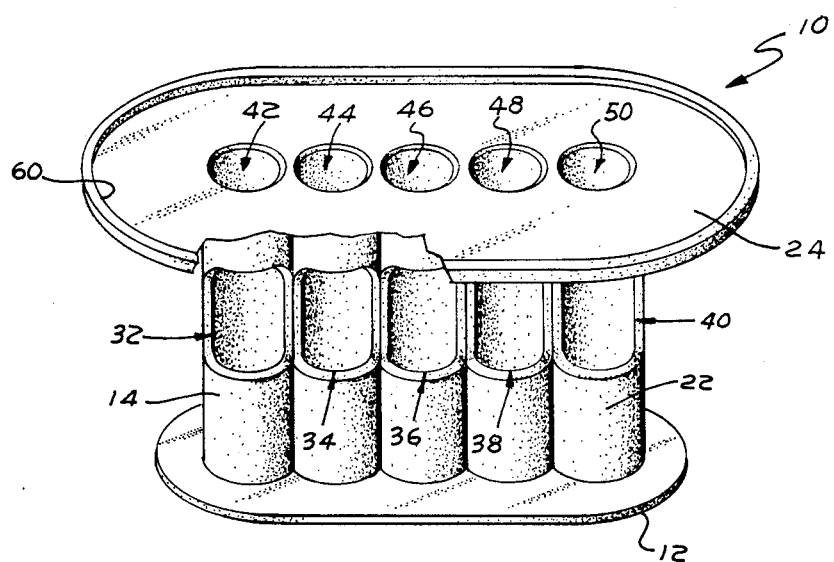
FIGS. 1 is a fragmentary top perspective view of a test-tube holder constructed in accordance with the present invention.
Figure 2:
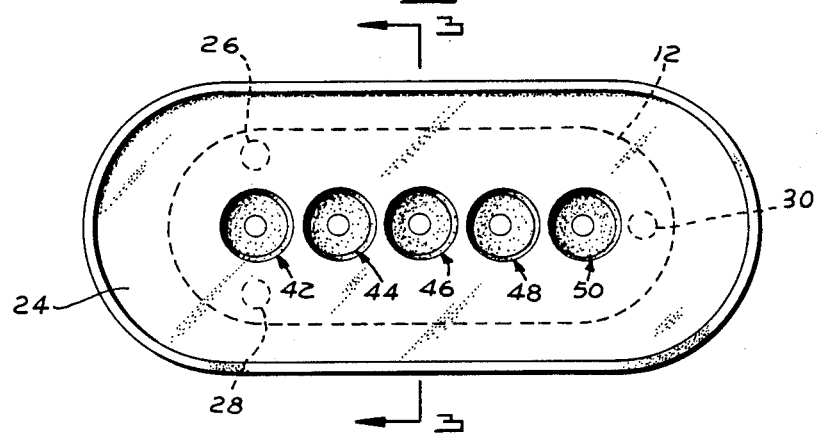
FIG. 2 is a top plan view of the test-tube holder.

Referring to the drawings in detail, the preferred embodiment of a test-tube holder or rack is shown and generally designated by the reference numeral 10 (see FIG. 1). The preferred embodiment is comprised of three main parts: an oval base 12; a row of vertical shafts 14, 16, 18, 20, 22 for holding or storing vials; and an overlying, oval top 24 which acts as a protective shield for the user who grasps the vertical shafts.

The base 12 is designed of any suitable plastic, such as the acrylonitrile butadiene styrene ("ABS resin") marketed by DuPont Co. of Wilmington, DE. Similarly, all other components of the test-tube rack 10 are made of this same material.

Base 12 is designed to allow the entire test-tube holder 10 to stand independently. It has three small "balancing" pads 26, 28, 30 integrally formed on its bottom, to ensure stability. These "balancing" pads are necessary due to a tiny "draft angle" on the base's bottom surface (not shown on the drawings). That angle makes it easier to remove the holder from the mold in which it is formed.

The shaft 14, 16, 18, 20, 22 are integral with the base 12 and extend vertically therefrom. Each shaft contains a corresponding frontal slot, as shown at 32, 34, 36, 38, 40 in FIG. 1.

The top 24 is integral with, and perpendicular to, the vertical shafts 14, 16, 18, 20, 22. It has a series of holes 42, 44, 46, 48, 50 aligned with the vertical shafts. These holes allow test tubes or vials 52, 54 to be loosely inserted into the holder 10. It should be noted that the top 24 is designed to be wider than a user's cupped hand 56. This completely shields the user's hand 56 from being pricked by a needle 58 that might slip while the rack is being used. The top 24 also has a raised outer edge 60 (see FIG. 3) which acts as a barrier. This barrier will either stop the needle or deflect its path away from the user's hand.

Figure 5:
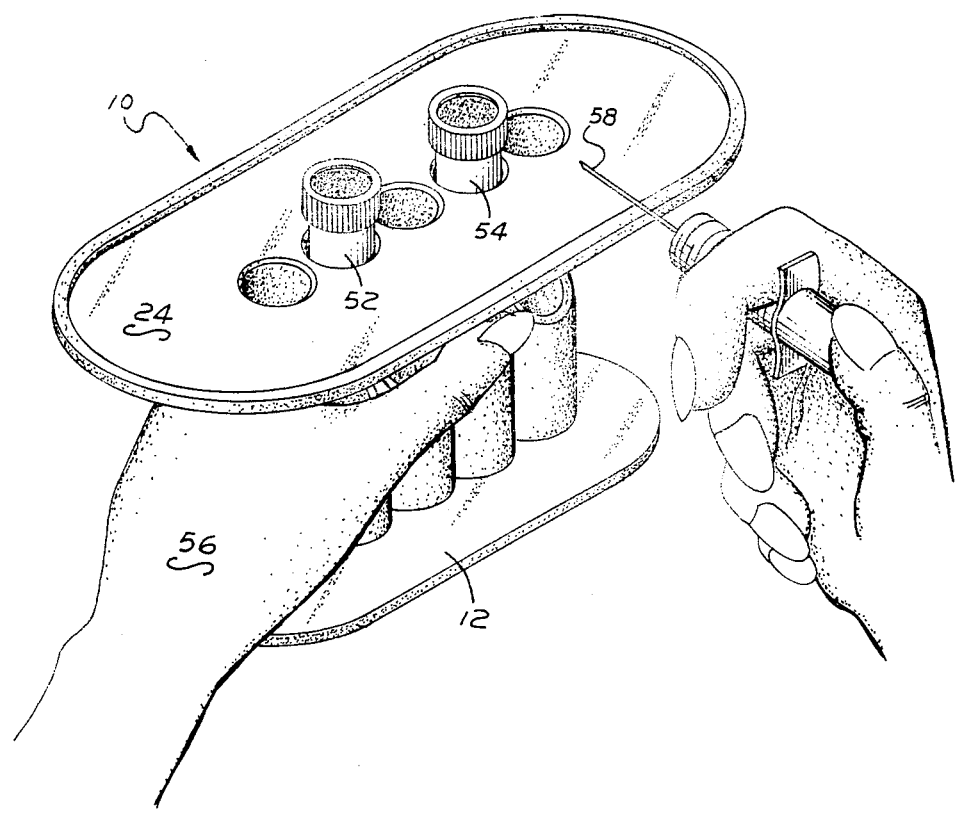
FIG. 5 is another top perspective view, similar to FIG. 4, showing a user actually grasping the invention and approaching it with a menacing needle, just prior to the test-tube holder and needle being tilted toward one another for insertion of the needle into the vial.

FIGS. 4 and 5 show the operational use of the test-tube holder 10. First, the user typically receives one or multiple vials (e.g., 52, 54) with blood samples that may be infected with the AIDS virus. He then slips the vials into vertical shafts (e.g., 16, 20) via the holes (e.g., 44, 48). There, they are stored (as in FIG. 4) until the user needs to lift the holder and draw or deposit a sample.

When that has to be done, the user cups his hand 56 underneath the protective shield 24 with his fingers behind the vertical shafts 14, 16, 18, 20, 22 and with his thumb in front of them (see FIG. 5). The instrument is designed to be equally accessible to people who are left- and/or right-handed.

By stretching his thumb or moving his hand around the vertical shafts 14, 16, 18, 20, 22 the user will have access to all the frontal slots 32, 34, 36, 38, 40. Thus he is capable of holding any stored, sealed vial in place, so that the needle can be easily withdrawn from the vial's seal. Each slot is large enough to allow the user's thumb to enter and exit freely.

After choosing the vial, e.g., 52, from which to obtain a sample, the user places his thumb through the corresponding slot 34 and presses the vial against the back of that shaft 16. He attempts to remove a sample from that vial 52 by tilting the holder 10 and needle 58 toward one another (from the FIG. 5 position) and inserting the needle into the vial's top.

If he injects and removes the needle 58 correctly, he never runs the risk of a needle injury. If the user miscalculates, though, ordinarily he could potentially be pricked with the needle 58 and therefore expose himself to contracting AIDS. However, with this present invention, the user is constantly protected from inadvertent needle-pricks because his hand is at all times beneath the protective shield 24.

Kindly note that, for the sake of clarity and simplicity, the drawings have been shown as if the test-tube holder were of an opaque rather than clear plastic. However, applicant believes another preferred embodiment would be to design the holder with a clear plastic. If the holder were clear, it would give the user more assurance because he could actually see his hand protected by the shield. It also allows him to see exactly where the slots are so that he may readily access the vials through these slots.

It should be understood by those skilled in the art that obvious modifications can be made without departing from the spirit of the invention. For example, the preferred embodiments are formed by injection molding. They could, of course, be made by hand. Accordingly, refernece should be made primarily to the accompanying claims, rather than the foregoing specifications, to determine the scope of the invention.

Having thus described the invention, what is claimed is:

1. A hand-held test-tube holder comprising:
 a. a horizontal base;
 b. a row of tubular shafts that are integral with the base and which extend vertically therefrom, wherein the shafts are each adapted in size and shape to house a test tube; and
 c. an overlying horizontal top that is integral with the shafts wider than a user's cupped hand which grasps the shafts to lift the holder, whereby the top acts as a shield to prevent that hand from being accidentally nicked by a needle when a sample is attempted to be drawn from the test tube, or deposited therein.

2. The test-tube holder of claim 1 wherein each shaft has a frontal slot, which allows a user to press the thumb of his cupped hand against a housed test tube to hold it in place.

3. The test-tube holder of claim 1 wherein the top has a series of holes that overlie the shafts to allow test tubes to be inserted into the shafts.

4. The test-tube holder of claim 2 wherein the holder is made of clear plastic, which permits a user to see his cupped hand and easily manipulated his thumb against a housed test tube.

5. A hand-held test-tube holder comprising:
 a. an elongated base that extends horizontally;
 b. a plurality of parallel tubular shafts that are integral with the base and which extend vertically therefrom, wherein each shaft is shorter than a test tube yet wide enough to loosely house that tube within it;
 c. an elongated top that overlies and extends horizontally above the shafts and which is integrally attached to them, said top having a series of holes that align with the shafts to allow test tubes to be inserted into the holder; and
 d. wherein the top is wider and longer than a user's cupped hand which grasps the shafts to lift the holder, whereby the top acts as a cover to prevent that hand from being accidentally nicked by a needle when a sample is attempted to be drawn from the test tube, or deposited in it.

6. The test-tube holder of claim 5 wherein each shaft has a frontal slot, which allows a user to press the thumb of his cupped hand against a housed test tube to hold it in place.

7. The test-tube holder of claim 6 wherein the holder is made of clear plastic, which permits a user to see his cupped hand and easily manipulate his thumb against a housed test tube.

* * * * *